United States Patent [19]

Romelli et al.

[11] Patent Number: 5,382,530

[45] Date of Patent: Jan. 17, 1995

[54] METHOD FOR THE QUANTITATIVE DETERMINATION OF A FREE FORM OF SUBSTANCES PRESENT IN BIOLOGICAL FLUIDS

[75] Inventors: Pier B. Romelli, Rho; Giovanni Chiodoni, Vaprio d'Adda; Roberto Ringhini, Cassina De' Pecchi, all of Italy

[73] Assignee: Technogenetics S.R.L., Milan, Italy

[21] Appl. No.: 997,735

[22] Filed: Dec. 30, 1992

[30] Foreign Application Priority Data

Apr. 14, 1992 [IT] Italy .......................... MI 92A000910

[51] Int. Cl.$^6$ .................. G01N 33/50; G01N 33/543; G01N 33/566; G01N 33/58
[52] U.S. Cl. ..................................... 436/500; 436/518; 436/825; 435/7.92; 435/7.93
[58] Field of Search ....................... 436/500, 501, 518; 435/7.1, 7.12, 47.13

[56] References Cited

U.S. PATENT DOCUMENTS

| | | | |
|---|---|---|---|
| 3,776,698 | 12/1973 | Eisentrut | 436/500 |
| 4,111,656 | 9/1978 | Margherita | 436/500 |
| 4,225,574 | 9/1980 | Romelli et al. | 436/500 |
| 4,347,058 | 8/1982 | Polito et al. | 436/500 |
| 4,745,072 | 5/1988 | Ekins et al. | 436/500 |
| 4,771,008 | 9/1988 | Miura et al. | 436/500 |
| 5,036,115 | 11/1991 | Hu et al. | 436/500 |

FOREIGN PATENT DOCUMENTS 0324540  7/1989  European Pat. Off. .

OTHER PUBLICATIONS

Copy of European Search Report EP 93 10 5327.

*Primary Examiner*—Christine M. Nucker
*Assistant Examiner*—Chris Dubrule
*Attorney, Agent, or Firm*—Darby & Darby

[57] ABSTRACT

Disclosed is a method for the direct determination of the free fraction of analytes present in biological fluids in a free form and in a form bound to one or more endogenous ligands (said free and bound forms being in equilibrium with one another). This method provides for a (preferably substantially simultaneous) use: a first ligand L1 capable of sequestering an analyte quantity proportionate to the free-analyte concentration present in a biological fluid and to subsequently release it, after removal from the biological fluid of the specific endogenous ligand, as a result of the addition of an appropriate selective dissociating agent; a second ligand capable of binding both the previously released analyte and a labelled version of the analyte, even in the presence of the dissociating agent; a selective dissociating agent; and a quantity of labelled analyte. The measured level of the labelled analyte which binds to the second exogenous ligand (or which remains unbound) is used to determine the concentration of the free analyte in the fluid.

12 Claims, No Drawings

METHOD FOR THE QUANTITATIVE DETERMINATION OF A FREE FORM OF SUBSTANCES PRESENT IN BIOLOGICAL FLUIDS

FIELD OF THE INVENTION

This invention relates to a method for the direct determination of the free form fraction of organic substances which are present in biological fluids both in a free form and in a form bound to one or more endogenous ligands, the two forms being in equilibrium. Examples of such endogenous ligands include without limitation proteins commonly present in said fluids. Examples of the foregoing organic substances, which shall hereinafter be generally called analytes, are various hormones, including but not limited to T3 and T4.

BACKGROUND OF THE INVENTION

Some physiologically active substances which are present in biological fluids (e.g. in blood) are balanced between a free form and a form bound to endogenous ligands present in the same fluids. For these substances, the free-portion level is generally known to be clinically more significant than the total-substance level. Only the free form is in fact responsible for biological activity. Observations made on both normal and pathologically afflicted humans confirmed that the variations observed in free-form concentrations more closely correlate to the patients' clinical condition than are those of the entire substance. This is particularly true of thyroid and steroid hormones (Robbins J. and Rall J. E., *Recent Progr. Hormone Res.*, 13:161 (1957); Robbins J. and Rall J. E., *Physiol. Rev.*, 40:415 (1960)).

Methods intended to measure the free portions of these hormones have long been known.

In the specific case of thyroxine (T4), early attempts to measure the free portion involved determining its total concentration, as described in U.S. Pat. No. 3,659,104, and then determining triiodothyronine (T3) uptake (U.S. Pat. No. 3,710,117), or effecting a complete T4 dissociation in the presence of labelled T4, followed by adsorption of the latter upon a resin and subsequent elution from the resin using a portion of the test serum (U.S. Pat. No. 3,941,564).

However, these methods can only provide a rough and often incorrect assessment of the free portion.

A need thus arose to find other methods in which the measured level is directly correlated to the free-analyte concentration or to its distribution between free and bound portions.

In principle, this objective can be achieved by introducing a new exogenous component and having it take part in the existing equilibrium between the free analyte form and the bound analyte form, which component should have the following characteristics:

a. be incapable of affecting substantially the free analyte fraction present in a sample of biological fluid;
b. be capable of sequestering an analyte quantity directly correlated to the free portion;
c. be easily separated from the other components which take part in the equilibrium.

The U.S. Pat. No. 4,225,574 describes an assay method for the determination of free analytes in biological fluids which is based on these principles.

Said method calls for a sample to be subjected to a chromatographic adsorption process using Sephadex LH-20 columns. As soon as the free analyte present in the sample is adsorbed upon the resin, its concentration in the sample is promptly restored by dissociation of the analyte from the bound portion. This adsorption and dissociation process continues until a balanced state between adsorbed analyte and free analyte in solution is reached. The quantity of adsorbed analyte is proportionate to the free-analyte concentration, and it is therefore possible to find the latter by determining the adsorbed quantity by radioimmunoassay and dividing it by the proportionality constant. This method is difficult to perform for the same reasons as all "two-step" methods (see below).

A variation, which is described in Belgian Patent BE 878687, uses an analyte-specific antibody as a sequestering agent in place of a resin. When said antibody is introduced into a fluid, in a quantity incapable of substantially upsetting the free-analyte/bound-analyte equilibrium present in the sample, the number of antibody-binding sites which are occupied by the analyte is proportionate to the free-analyte concentration present. The number of free sites is measured after removing endogenous carrier proteins by washing and then adding a labelled analyte which enables the free-analyte concentration to be determined.

The main drawback of the Belgian patent technique is the necessity to use an antibody with a very high affinity constant for the analyte. The sensitivity of this type of assay does not change in relation to the quantity of antibody used, but depends exclusively on its affinity constant. For instance: to obtain a satisfactory sensitivity when measuring free T4 an antibody with an affinity constant higher than $5 \times 10^{10}$ L/mol is required. On the other hand, if one wants to determine with acceptable sensitivity the concentration of free T3, which is present in blood in a lower concentration than T4, antibodies with an even higher affinity constant will be required.

The last two methods described are based essentially on a two-step sequential incubation: sequestration and then measurement.

The European Patent Application EP 26103 describes a method for assay of free analytes which tries to avoid this two-step sequential incubation by adding an appropriately labelled analyte derivative called "analogue" to the test sample at the same time as the analyte sequestering agent (analyte-specific antibody). If a particular analogue can be selected which is capable of binding to the sequestering agent but incapable of binding to the natural ligands present in biological fluids and is, therefore, only capable of competing with the available free-analyte moiety in binding to the antibody, the level of the antibody-bound signal will change only in proportion to the free-analyte concentration in the biological fluid.

In the method described in the European Patent Application EP 89806, which is similar to the preceding one, the specific ligand is labelled, instead of the analyte derivative. The analyte and its derivative compete for binding to the labelled specific ligand and the measured level of specific ligand bound to the analyte derivative is used to determine the free analyte concentration.

The methods, such as the one above, which use an analyte derivative (so called "one-step" methods) are extremely easy to carry out, which makes them more usable for laboratory routine than the methods in which the sequestering step is separate from the measuring step (so called "two-step" methods).

However, a serious drawback in the "one step" methods which use the "analogue" technique is the fact that it is not easy to select such a particular reagent, as it tends to bind to the natural ligands which are constantly present in biological fluids. When this occurs, the measured level is affected by the concentration of said ligands present in the sample.

Thus far it has not been possible to obtain a derivative which was thoroughly free from this drawback, the results obtained by these methods did not prove sufficiently reliable. The largest discrepancies occur in the cases where the quantity and quality (e.g., as a result of genetic alteration) of the natural ligands are far from normal (Refetoff, S. Endocr. Rev. 10:275, 1989; Waltz, M. R., J. Endocrinol. Invest. 13:343, 1990) or when substances are co-present that may affect the equilibria (between free and bound analyte) present in the biological fluids, such as for instance: nonesterified fatty acids, drugs used by patients under treatment and all the substances which bind in particular to albumin (Stockigt J. R. et al., Clin. Endocrinol., 15:313 (1981); Bayer M. F., Clin. Chim. Acta, 130:391, (1983); Beck-Peccoz P. et al., "Free T4 and free T3 measurement in patients with antiiodothyronine autoantibodies" in: Albertini A., Ekins R., Eds. "Free Hormone in Blood", 231: (1982), Amsterdam: Elsevier/North Holland).

In an attempt to avoid the above drawbacks, European Patent Application EP 155104 describes a method for free-analyte measurement in biological fluids, which uses, in addition to an analyte analogue, differential blocking agents which are intended to prevent or dissociate the bond between the analogue and natural ligands, in particular albumin. However, the addition of said differential blocking agents to the sample to be measured substantially affects the free-analyte/bound-analyte equilibrium in the sample itself, which distorts the measured levels.

Based on what has been previously described, in the present state of the art:

(1) "two step" methods are more reliable than "one step" methods owing to the difficulty of finding an appropriate analogue for "one-step" methods;

(2) "two step" methods which use the same exogenous ligand both to sequester and to measure an analyte do not have the required sensitivity;

(3) "two step" methods (which use different techniques for the sequestering step than for the measuring step of a free analyte) entail difficult sample manipulations and are not practical for use in routine laboratory analyses. Examples are dialysis or adsorption or ultrafiltration for sequestering and immunoassay for measuring.

OBJECTS OF THE INVENTION

An object of the present invention is, therefore, to provide a method for the determination of the free portion of analytes present in biological fluids, which provides a solution to at least one of the above-mentioned problems.

Another object is to provide a method that has the reliability of known "two step" methods, it has adequate sensitivity and is easy to perform using routine laboratory procedures.

The method of the invention can be used to measure the free-form concentration not only of analytes such as thyroid hormones (thyroxine and triiodothyronine) and steroid hormones (e.g. aldosterone, testosterone, cortisol), but also of all the substances which are present in biological fluids and have a bound form and a free form balanced with each other (e.g.: biochemical messengers, drugs and their metabolites, polypeptides and proteins, vitamins, polysaccharides, tumor antigens, toxins, alkaloids and the like).

SUMMARY OF THE INVENTION

The present method for determining the amount of an analyte (A) present in a biological fluid in free form comprises the following elements:

(a) a first exogenous ligand (L1) capable of sequestering an analyte quantity correlated to the free portion present in a biological fluid;

(b) a dissociating agent (D) capable of dissociasing the sequestered analyte from the first exogenous ligand;

(c) a labelled form (M) of the analyte to be determined;

(d) a second exogenous ligand (L2) capable of proportionally binding both the dissociated analyte and the labelled analyte (M) even in the presence of the dissociating agent (D);

(e) a set of standard solutions (SS) made up of sera containing known quantities (e.g., serial dilutions) of total analyte (free+bound) for which the free analyte concentrations are known.

The method is implemented by a "competitive" assay system where both exogenous ligands L1 and L2 are simultaneously present and easy to separate from the other reaction components.

DETAILED DESCRIPTION OF THE INVENTION

The use of a first exogenous ligand (L1) capable of sequestering an analyte quantity proportionate to the free-analyte concentration present in a biological fluid and then to release said quantity pursuant to the action of the dissociating agent (D), makes it possible to obtain a higher sensitivity than that of methods which use the same ligand in both the sequestering step and the measuring step, because the first specific ligand is not involved in the subsequent (detecting) reaction (analyte+labelled analyte+second specific ligand). The quantity of the second specific ligand may, therefore, be kept lower than the quantities of the labelled analyte and of the sequestered analyte in the prior art methods. This results in higher sensitivity of the present method compared to the common "two-step" assay methods which use the same specific antibody both in the sequestering and measuring steps.

The use of a dissociating agent (D) capable of releasing the sequestered analyte and not interfering with the competition reaction between dissociated analyte and labelled analyte in binding to the second exogenous ligand, allows both ligands to be simultaneously present during all the measuring stages, with consequent simplification of the operating procedure as compared to the prior art "two step" methods which use different systems or techniques in performing the sequestering step from those used in performing the measuring step.

The use of standard solutions comprising sera with known free-analyte concentrations is preferred as it enables the free-analyte concentration present in the sample to be determined even when the proportion existing between free-analyte concentrations and sequestered-analyte levels is not known. Importantly, the use of these solutions allows accurate measurement even under conditions which are not strictly standard.

For instance: a change in the free-analyte concentration present in the sample, caused by a change in incubation temperature, is normalized by comparison with values found in the in-vitro standard, the free-analyte concentration of which changes with temperature in the same manner.

The method of the present invention comprises the use of the following components:

A—an analyte to be determined;
L1—a first specific exogenous ligand, preferably bound to the surface of a stationary or dispersed solid phase;
L2—a second specific exogenous ligand, preferably bound to the surface of a stationary or dispersed solid phase;
M—a predetermined quantity of labelled analyte;
D—an agent capable of dissociating the analyte A from the first exogenous ligand L1, without affecting the ability of the second exogenous ligand L2 to bind to said analyte and to the labelled analyte M;
SS—a set of standards comprising, e.g., solutions or sera with known free-analyte concentrations or a set of standard concentration values (e.g., in table or graph form).

In order not to affect the system equilibria so significantly as to cause measurement distortions, ligands L1 and L2 are present in quantities incapable of changing to any significant extent (e.g., keep the change to no more than 10%) the concentration of the free analyte A present in the biological fluid and, in particular, the second ligand L2 is deficient compared to the quantity of the labelled analyte M (e.g., no more than enough L2 to bind about 50–60% of M). To determine the appropriate amount of L1 and L2, the percentage of the sequestered analyte compared with total analyte must be evaluated. This percentage roughly correlates with the percentage decrease of the free analyte concentration due to the presence of the "new" ligands L1 and L2 in the system (See, *Ligand Quarterly*, 8 (Suppl. to No. 1), 1989).

The first exogenous ligand L1 is selected among those capable of sequestering the analyte A without substantial interference from any other substances which might compete with the analyte binding to L1. (This means that L1 binds A quantitatively with relatively high affinity and with specificity.) The amount of the sequestered analyte A is thus proportionate only to the concentration of the free analyte A.

The analyte A present in the biological fluid also binds to the second exogenous ligand L2, but to a lower extent quantitatively before dissociation takes place. Thus, L1 and L2 are chosen so that e.g., only a certain amount of analyte binds to L2 and a multiple of that amount (e.g., 2–5 times) is bound to L1. This can be ascertained beforehand using, e.g., labelled analyte M and can be accomplished either by choice of relative affinities of L1 and L2 for A or by choice of the relative quantities of these exogenous ligands, or both. Although, theoretically, the greater the affinity of L2 for A and/or the smaller the quantity of L2, the greater the sensitivity of the assay, in practice L2 has to have sufficient affinity for A to produce a differential "reading" in the assay and for the same reason must be present in a sufficiently high quantity. In any case the sequestered quantity of the analyte initially bound to L2 is also proportionate to the concentration of the free analyte and therefore easily standardized.

The dissociating agent (D), which dissociates the analyte A from the first ligand L1, may be either a substance capable of successfully competing with the analyte A in binding to the same site(s) of the first exogenous ligand L1, but not to those of the second exogenous ligand L2, or an agent capable, because of its physico-chemical characteristics, to weaken considerably the bond between the analyte A and the first ligand L1 without, however, substantially affecting the affinity characteristics of the second specific ligand L2 for the analyte. In the latter case, in the presence of D, the binding affinity of L1 for A should be at least 100 times lower than the binding affinity of L1 for A, when D is not present. Relative affinity characteristics can be worked out as a function of the equilibria and substances involved using commercially available software such as EUREKA, available from Real Software, Sequel, Calif.

The use of a solid phase as a support for the exogenous ligands allows, after the sequestering step, a rapid and easy removal of the natural ligands present in the sample and a simple and rapid separation, during the measuring step, of the labelled analyte bound to the second exogenous ligand from the still-free labelled analyte. Precipitation of L2 complexes is another of the possible alternatives for separation from the natural ligands but use of a solid phase support is preferred.

The solid phase may be stationary, e.g., the walls of the very container in which the determination takes place, such as for instance: test tubes of polystyrene, polypropylene and any other material capable of causing adhesion of exogenous ligands. Alternatively, the solid phase may be suspended, e.g., consist of appropriate elements which serve to increase the usable surface area (such as beads). These elements are introduced into the container and can be made of the same materials as illustrated above. These materials are commercially available, e.g., from Pierce Chemical Co., Richford, Ill. and Precision Plastic Ball Co., Chicago, Ill. Another type of support that can be used is, e.g. that used in ELSA (TM) Solid Phase from Int'l CIS, Gif-Sur-Yvette, France.

The solid phase may also be dispersed, as is the case, for instance, when using cellulose microelements or the like which may then be separated by centrifugation, by the action of a magnetic field or by any other technique which makes use of their typical physico-chemical properties, such as chromatography columns.

The advantage of a stationary solid phase is that it can be more easily separated from the reaction mixture during determination. The advantage of a dispersed solid phase is that it has a larger surface available to fix exogenous ligands. Choice between them is within the skill in the art.

The exogenous ligands may be selected either among natural binding proteins, such as (in the case of thyroxin measurements) TBG (thyroxin binding globulin), transcortin, specific receptors and the like, or among analogues thereof obtained e.g. by DNA recombinant techniques and the like. Polyclonal as well as monoclonal analyte-specific antibodies can also be exogenous ligands. Analyte specific antibodies can easily be produced by well-known methods. Nonlimiting examples of ligands can be found, e.g., in Weeks; Avrameas; Ishikawa; Hunter, all of them infra.

Fixation of ligands L1 and L2 to the solid phase may be direct or indirect. Indirect fixation involves binding to the solid phase by known techniques a molecular species which has an affinity for a specific tracer (label) which in turn is fixed to a ligand. For example, the sequence (solid phase)-(streptavidin)/(biotin)-(ligand) or (solid phase)-(antifluorescein antibody)/(fluorescein)-(ligand) can be used.

When the ligand (L1 and/or L2) is an antibody, it can also be fixed to the solid phase by the use of anti-antibody antibodies, e.g.: (solid phase)-(anti-rabbit gamma globulin)/(anti-analyte antibody produced in rabbits).

The two exogenous ligands used may be bound to one or more different solid phases using either the same method or different methods.

To provide the labelled analyte M one may resort to the usual techniques well-known to those skilled in the art and described in the literature, which include: labelling with a radioactive atom (for instance $^{125}I$), labelling with enzymes or components of enzyme systems and labelling with chemiluminescent or fluorescent groups such as for instance acridinium or fluorescein esters. See, e.g., Weeks, I. et al. *Clin. Endocrinol.* 20:489, 1984; Avrameas, S. *Immunochem.* 6:43, 1969; Ishikawa, E. *Develop. Immunol.* 18:219, 1983; Hunter, W. M. *Nature* 194:495, 1962. In general, any material that can bind firmly to the analyte and that can be detected can be used as a label.

Substances that function as selective dissociating agents may be found among synthetic or natural compounds with structures capable of giving them a binding affinity only for the first exogenous ligand. For instance, in the case of the analyte T4, this substance may be selected in a group including 8-anilino-1-naphthalenesulphonic acid (ANSA), sodium salicylate, sodium ethyl-[2-mercaptobenzoate(2-)-O,S]-mercurate(1-) (Thimerosal) and the like.

Alternatively, when the dissociating function is based on physico-chemical characteristics, such characteristics may include:pH, ionic strength, temperature and generally any variable capable of loosening binding forces. An example of the use of such agent in the form of a solution is described in Example 2.

The above mentioned dissociating agent and labelled analyte may both be present in the same solution, in order to further simplify the measuring process.

Described below are two examples of determinations of free thyroxine (T4) and free triiodothyronine (T3) in human serum, which are merely intended to better explain the applicability of the invention and shall in no way be considered a limitation thereof.

T3 and T4 are known to circulate in blood mainly in a protein-bound form, but a free portion of these hormones is also known to be present in blood and is found to be in thermodynamic equilibrium with the bound portion.

In the case of T4, this hormone is bound to the extent of about 70% to thyroxine binding globulin (TBG), about to thyroxine binding prealbumin (TBPA) and about 10% to albumin.

The free T4 in blood is approximately 0.02–0.03% of the total hormone concentration.

T3 is carried by the carrier proteins themselves (TBG:60%, TBPA:15%, albumin:25%), while the free form accounts for about 0.3% of the total hormone concentration.

To prepare the components of the following assay systems the following materials were used and are listed with commercial suppliers:

12×75 mm "MAXYSORP" polystyrene test tubes (NUNC, Roskilde, Denmark]

human thyroxine binding globulin (TBG) (Boehringer, Mannheim, Germany)

monosodium phosphate, disodium phosphate, sodium azide, sodium chloride, TRIS (tris-(hydroxymethyl) aminomethane), potassium chloride, calcium chloride, magnesium sulphate, pure, analytical grade (Merck, Darmstad, Germany)

Streptavidin from *Streptomyces avidinii*, N-succinimide ester of biotinyl-E-aminocaproic acid (SPA, Milan, Italy)

ANSA (magnesium salt of 8-anilino-1-napththalenesulphonic acid), gelatin for microbiology, HEPES (4-(2-hydroxyethyl)-1-piperazinyl) ethanesulphonic acid), HEPES sodium salt, thyroxine (T4), 3,3', 5-triiodothyronine (T3) (SIGMA, St Louis, Missouri).

EXAMPLE 1

DETERMINATION OF FREE T4

1. Preparation of the Components of the Assay System

The solid phase, which consisted of 12×75 mm polystyrene test tubes with both the exogenous ligand L1 (TBG) and the exogenous ligand L2 (anti-thyroxine antibody produced in rabbits) adhering to their inner surfaces, was prepared using the following operating procedure:

1 mL of 0.05M phosphate buffer at pH 7.5 containing 5 μg/mL of streptavidin and 4 μg/mL of anti-rabbit gamma globulin antibody are added to each test tube.

After incubation for 18–24 hours at room temperature, the solution present is removed by suction and each test tube is washed with 1 mL of 0.05M phosphate buffer at pH 7.5 and 0.1% sodium azide.

1 mL of 0.05M phosphate buffer at pH 7.5 containing 1 μg/ml of biotinylated TBG (ligand L1-biotin), 150 ng/mL of anti-T4 antibody (ligand L2) and 0.1% sodium azide is added and the whole is incubated for 18–24 hours at room temperature. During incubation the biotinylated TBG and the antibody bind respectively to streptavidin and to the anti-rabbit gamma globulin antibody previously adsorbed upon the test tube internal walls.

At the end, the solution present is removed by suction and each test tube is washed with 1 ml of 0.05M phosphate buffer at pH 7.5 containing 1% gelatin and 0.1% sodium azide.

The rabbit anti-rabbit gamma globulin antibody and the anti-T4 antibody (produced in rabbits) were prepared using methods well known to those skilled in the art and described in the literature. Vaitukaitis, G. G. *Clin. Endocr.* 33:988, 1971; Chapman, R. S. in Hunter, W. M. "*Immunoassays for Clinical Chemistry*", p. 456, 1983, Churchill et al. Eds, Edinburgh (U.K.); Marguerita, S. *Experientia* 37:314, 1981. The two antisera produced were then purified, the former by affinity chromatography, the latter by specific gamma-globulin precipitation with ammonium sulphate. Such antibodies are also commercially available, e.g. from Boehringer Mannheim, Mannheim, Germany; or Scantibodies Lab. Inc., Santee, Calif.

The thyroxine binding globulin (TBG) was treated with biotin using biotin-hydroxysuccinimide ester and the extent of the biotin treatment was determined after ascertaining the relationship existing between the biotin/TBG ratio and the ability of the biotinylated binding protein to bind the analyte.

The ability of the biotinylated TBG to bind the analyte was evaluated by adding to the test tube, previously sensitized with constant quantities of TBG-biotin with different biotin/TBG ratios, 1 mL of a T4-$^{125}$I solution (100 pmol/L-specific activity: 2,000 μCi/μg) in 0.2M HEPES buffer at pH 7.4. After incubation for one hour at room temperature, shaking at 100–150 rpm, the radioactivity not bound to TBG was removed by suction and washing and the bound radioactivity was measured by a gamma-counter. The highest binding ability was obtained using a biotin/TBG ratio of about 3. (It is evident that once such a ratio has been optimized this step need not be performed.)

The labelled analyte (T4-$^{125}$I) was prepared using well known procedures and diluted in a dissociating solution made up of 0.05M TRIS buffer at pH 8.6 containing 0.02% ANSA, 0.1% gelatin and 0.1% sodium azide.

Standard (reference) solutions were prepared adding to a T4-free human serum (obtained from normal human serum, deprived of T4 by treatment with carbon-dextrane) respectively 15, 30, 50, 80, 120 ng/mL of T4.

The free-analyte concentration present in the solutions was determined using the equilibrium-dialysis reference method as described by Ellis S. M. and Ekins R. P.: "The radioimmunoassay of serum free triiodothyronine and thyroxine" in: "*Radioimmunoassay in Clinical Biochemistry*", page 187 (1975), Ed. C. A. Pasternak, Heyden N.Y.

2. Determination of the Free-T4 Concentration

Each of 200 μL of standard solution and 200 μL of a serum to be determined containing the analyte (A) are added respectively to a coated tube sensitized as described in Part 1 (i.e., having L1 and L2 adhering to their surface).

1 mL of 0.2M HEPES buffer at pH 7.4 containing 0.5% sodium chloride, 0,025% potassium chloride, 0.025% calcium chloride, 0.025% magnesium sulphate and 05% sodium azide, is then added to each tube.

After incubation for 1 hour at room temperature shaking at 100–150 rpm, the solution is thoroughly removed by suction or decantation and the test tubes are washed twice with 0.05M phosphate buffer at pH 7.5 containing 0.1% sodium azide.

1 mL of dissociating solution (D) containing 15 pmol/L of labelled analyte (M) (approximately 80,000 cpm-specific activity: 5,629 μCi/μg) is added to each test tube and, after incubation for 1 hour at room temperature shaking at 100–150 rpm, the reaction mixture is removed by suction or decantation and the radioactivity bound to the test tubes is measured by a gamma-counter.

the standard curve is calculated and the levels relative to the samples containing the serum to be determined are obtained by curve fitting. Table I shows an example of standard curve.

TABLE I

| Free T4: standard curve | |
|---|---|
| Free T4 (pmol/L) | Bound radioactivity (cpm) |
| 0.0 | 47,950 |
| 3.3 | 36,308 |
| 7.0 | 30,193 |
| 13.8 | 21,713 |
| 26.6 | 15,093 |

TABLE I-continued

| Free T4: standard curve | |
|---|---|
| Free T4 (pmol/L) | Bound radioactivity (cpm) |
| 56.9 | 10,643 |

3. Evaluation of the Efficacy of the Assay System

3a. Efficacy of the Dissociating Agent

The evaluation of the sequestering system and of the subsequent dissociation of the sequestered analyte was made using coated tubes sensitized with different known quantities of TBG (L1) in the absence of the anti-T4 antibody (L2), using the following trial protocol:

1 mL of labelled analyte (M) diluted in 0.2M HEPES buffer at pH 7.4 is added to each of a set of test tubes coated with different quantities of TBG (125, 250 and 500 ng/test tube).

After incubation for 1 hour at room temperature shaking at 100–150 rpm, the radioactive solution is decanted and the test tubes are washed twice with 1 mL of 0.05M phosphate buffer at pH 7.5 containing 0.1% sodium azide.

The radioactivity still bound to the test tubes, due to radioactive T4 sequestered by TBG in the solid phase, is measured by a gamma-counter.

After the count, 1 mL of a dissociating solution (D) consisting of 0.05M TRIS buffer at pH 8.6 containing 0.02% ANSA is added to each test tube.

After incubation for 15 minutes at room temperature, the added solution is removed by suction and, after washing with 1 mL of 0.05M phosphate buffer at pH 7.5 containing 0.1% sodium azide, the test tubes are again measured by a gamma-counter.

The last radioactivity measured correlates to the quantity of non-dissociated radioactive analyte.

Each determination was made in quintuplicate and the mean values obtained are shown in Table II with the respective percentages of sequestered analyte and dissociated analyte.

TABLE II

| Free T4: Evaluation of the Dissociating Solution | | | | | |
|---|---|---|---|---|---|
| | THYROXINE BINDING GLOBULIN (ng/test tube) | | | | |
| | 125 | | 250 | | 500 |
| T4-$^{125}$I | (cpm) | (%) | (cpm) | (%) | (cpm) | (%) |
| a) added | 240,312 | 100.0 | 239,987 | 100.0 | 243,252 | 100.0 |
| b) sequestered | 161,718 | 67.3 | 212,916 | 88.7 | 222,846 | 91.6 |
| c) residue | 900 | — | 1,208 | — | 1,027 | — |
| b-c/b dissociated | — | 99.4 | — | 99.4 | — | 99.5 |

The results obtained show that the action of the dissociating solution enables nearly all the sequestered analyte (>99%) to be released from TBG.

3b. Effect of the Dissociating Agent on the Second Exogenous Ligand

The effect of the dissociating agent on the anti-T4-antibody activity was evaluated by comparing the quantities of labelled analyte sequestered by the solid phase in the presence of progressively higher known quantities of dissociating agent and using test tubes coated only with the antibody (Table III).

The results obtained demonstrate that the dissociating agent, at the concentration used (0.02% ANSA), does not affect substantially the antibody binding ability. The decrease in bound T4-$^{125}$I is about 4.9% as seen in Table III. A decrease of about 10% or more would be substantial.

TABLE III

Free T4: Effect of the Dissociating Agent

| ANSA (%) | Bound T4-$^{125}$I (cpm) |
|---|---|
| 0.000 | 13,708 |
| 0.003 | 13,872 |
| 0.006 | 12,925 |
| 0.012 | 13,178 |
| 0.025 | 13,032 |
| 0.050 | 12,875 |
| 0.100 | 12,462 |
| 0.200 | 11,189 |

3c. Validity Test for the Measuring Method

The validity of the method developed was demonstrated by:
- determining the free-T4 concentration after addition either of constant volumes (200 μL) of serum at different known dilutions, or of different known volumes of undiluted serum;
- comparing the free-T4 values obtained in 62 serum samples from euthyroid patients or thyreopathic patients by a known method used as a reference.

Since it is known that a dilution of the serum by a few orders of magnitude has a negligible effect on free-T4 concentration (Romelli P. B. et al., *J. Endocrinol. Invest.*, 2:25 (1979)), the determinations obtained in a sample at different dilutions make it possible to ascertain whether a determination method is capable of measuring the free-T4 portion without being affected by a change in carrier protein concentration. If dilutions affected free analyte concentration, either higher volumes of undiluted serum or a lower quantity of L1 would have to be used.

Table IV a) shows the results obtained in the dilution test which was carried out by adding to the solid phase 200 μL of sample at different known dilutions. Table IV b) shows the results obtained by adding to the solid phase different known volumes of the same sample.

Different human sera (A, B, C, D) were used in the two tests. The results obtained demonstrate that the method is capable of measuring correctly the free T4 concentration without being affected by changes in endogenous ligand concentration.

TABLE IV a)

Free T4: Effect of Sample Dilution

| Sample | Dilution | Free T4 (pmol/L) |
|---|---|---|
| A | — | 8.82 |
|   | 1:2 | 8.47 |
|   | 1:4 | 9.07 |
|   | 1:8 | 8.78 |
| B | — | 7.98 |
|   | 1:2 | 8.39 |
|   | 1:4 | 8.23 |
|   | 1:8 | 8.13 |

TABLE IV b)

Free T4: Effect of Volume

| Sample | Volume (μL) | Free T4 (pmol/L) |
|---|---|---|
| C | 400 | 14.22 |
|   | 200 | 14.52 |
|   | 100 | 14.11 |
| D | 400 | 15.89 |
|   | 200 | 15.58 |

TABLE IV b)-continued

Free T4: Effect of Volume

| Sample | Volume (μL) | Free T4 (pmol/L) |
|---|---|---|
|   | 100 | 14.56 |

The clinical validity of the method which is an object of the invention was confirmed comparing the results obtained with those obtained by the method described in the U.S. Pat. No. 4,225,574 considered as a reference.

The values obtained by the invention method (y) are comparable with those obtained by the reference method (x).

The comparison was evaluated by statistical analysis of the linear regression, which gave the following results: y=0.7+1.05 x, coefficient of correlation r=0.997.

4. Comparison of the Sensitivity with the One-ligand Method

Table V shows the results relative to a standard curve obtained using the same specific antibody L2 in both the sequestering and measuring steps (Method A), and compares them with those obtained by the method which is an object of the present invention (Method B), which uses two different ligand systems, one for sequestration (TBG) and the other for measurement (antibody) L2.

The increased sensitivity determined by the use of two different ligands is evident from Table V.

TABLE V

Free T4: Effect of the Sequestering Ligand

| | Bound radioactivity | |
|---|---|---|
| Free T4 (pmol/L) | Method A (cpm) | Method B (cpm) |
| 0.0 | 46,526 | 47,950 |
| 3.3 | 37,646 | 36,308 |
| 7.0 | 32,575 | 30,193 |
| 13.8 | 30,223 | 21,713 |
| 26.6 | 27,309 | 15,093 |
| 56.9 | 24,475 | 10,643 |

EXAMPLE 2

DETERMINATION OF FREE T3

1. Preparation of the Components of the Assay System

The solid phase, which consisted of 12×75 mm polystyrene test tubes with the two exogenous ligands (L1 and L2) adhering to their inner surfaces was prepared using the following operating procedure:

1 mL of 0.05M phosphate buffer at pH 7.5 containing 3 μg/mL of anti-mouse gamma globulin antibody and 2 μg/mL of anti-rabbit gamma globulin antibody is added to each test tube and the test tubes are incubated for 18–24 hours at room temperature.

The obtained solution is removed by suction and each test tube is washed with 1 mL of 0.05M phosphate buffer at pH 7.5 containing 0.1% sodium azide.

1 mL of 0.05M phosphate buffer at pH 7.5 containing 1 μg/mL of monoclonal anti-T3 antibody produced in mouse (first exogenous ligand L1), 100 ng/mL of polyclonal anti-T3 antibody produced in rabbits (second exogenous ligand L2) and 0.1% sodium azide is added to each test tube and the test tubes are incubated for 18–24 hours at room temperature.

During incubation the monoclonal anti-T3 antibody and the polyclonal anti-T3 antibody bind respectively to the anti-mouse gamma globulin antibody and to the anti-rabbit gamma globulin antibody previously bound to the test tube inner walls.

The obtained solution is removed by suction and the test tubes are washed with 1 mL of 0.05M phosphate buffer at pH 7.5 containing 1% gelatin and 0.1% sodium azide.

The labelled analyte (T3-$^{125}$I), prepared using well known procedures, was diluted in 0.1M citrate buffer at pH 3.5 containing 0.1% gelatin and 0.1% sodium azide.

Operating in the 3.0–3.5 pH range or anyhow at pH values lower than 4 caused a considerable reduction of the affinity constant of the sequestering antibody, without changing the binding characteristics of the anti-T3 antibody used in the assay.

In the new equilibrium established in the new environment between sequestered analyte, labelled analyte and the two specific ligands the two analyte forms (sequestered and labelled) compete for binding sites of the polyclonal antibody.

Table VI shows the results related to T3-$^{125}$I binding, under different pH conditions, to the two antibodies used.

TABLE VI

Free T3: Effect of pH

| pH | Bound radioactivity (cpm) | |
|---|---|---|
|  | Polyclonal ab (L2) | Monoclonal ab (L1) |
| 3.0 | 11,360 | 2,451 |
| 3.5 | 13,637 | 3,209 |
| 4.0 | 13,421 | 6,720 |
| 5.0 | 12,942 | 10,569 |
| 7.0 | 13,890 | 12,611 |
| 8.0 | 13,219 | 12,726 |
| 9.0 | 12,011 | 12,100 |

These results evidence the different behaviors of the two antibodies, in fact the measuring antibody (L2) maintained a substantially constant ability to bind T3-$^{125}$I from pH 3 to pH 9, whereas the sequestering antibody (L1) at a more acid pH (4 or lower) showed a considerably reduced binding ability.

The standard solutions were prepared adding scalar quantities respectively of 0.15, 0.36, 0.77, 1.05, 3.75 ng/mL of T3 to a T3-free human serum obtained from normal human serum previously deprived of T3 by treatment with carbon-dextrane.

The free-T3 concentration present in the solutions was determined using the reference method described in the U.S. Pat. No. 4,255,574.

2. Determination of the Free-T3 Concentration

The determination of the free-T3 concentration calls for the following procedure:

Standard sera or unknown sera (500 μL each) are added respectively to a coated tube.

500 μL of 0.2M HEPES buffer at pH 7.4 containing 0.5% sodium chloride, 0,025% potassium chloride, 0.025% calcium chloride, 0,025% magnesium sulphate and 0.05% sodium azide are then added.

After incubation for 1 hour at room temperature shaking at 100–150 rpm, the reaction mixture is removed by suction or decantation and the test tubes are washed twice with 0.05M phosphate buffer at pH 7.5 containing 0.1% sodium azide.

1 mL of a dissociating solution made up of 0.1M citrate buffer at pH 3.5, 0.1% gelatin and 0.1% sodium azide, containing 8 pmol/L of labelled analyte (about 40,000 cpm-specific activity: 3,352 μCi/μg) is added to each test tube.

After incubation for 1 hour at room temperature shaking at 100–150 rpm, the reaction mixture is removed by suction or decantation and the radio-activity bound to the test tubes is measured by a gamma-counter.

The standard curve is calculated and the levels of unknown sera are obtained by curve fitting.

Table VII shows an example of standard curve.

TABLE VII

Free T3: Standard Curve

| Free T3 (pmol/L) | Bound radioactivity (cpm) |
|---|---|
| 0.0 | 12,822 |
| 2.0 | 11,987 |
| 3.1 | 11,580 |
| 8.3 | 9,387 |
| 15.7 | 6,889 |
| 28.3 | 4,896 |

EXAMPLE 3

A PREFERRED ASSAY KIT FOR MEASURING T4 AND INSTRUCTIONS FOR USE

Serum specimens can be tested without pre-treatment. They should be stored at 2°–8° C. for up to 24 hours prior to testing, or at −20° C. for up to 5 months. Testing should be at room temperature.

The assay reagents are:
1. Labelled Analyte and Dissociating Agent: $^{125}$I-T-4 (105 mL; L1) in 0.05 m Tris-EDTA buffer, pH 8.6, and also containing 0.02% ANSA (D), BSA, 0.1% sodium azide and red coloring.
2. Reaction Buffer: 60 mL.
3. L1/L2:50 polystyrene tubes (12×75 mm) are provided. They are coated with anti-T4 polyclonal antibody (L2) and TBG (L1) (same amounts as in Example 1). Uncoated tubes are also used to assay for $^{125}$I-T4 total activity.
4. Free T4 Standards for Calibration: These are supplied in labelled vials in freeze-dried form and include a "standard zero" and five standards containing 0.1% sodium azide and known amounts of T4 in serum, as follows:

| Standard | T4 (pg/mL) | T4 (pmol/L) |
|---|---|---|
| 0 | 0 | 0 |
| 1 | 3 | 3.9 |
| 2 | 6 | 7.7 |
| 3 | 12 | 15.4 |
| 4 | 25 | 32.2 |
| 5 | 50 | 64.4 |

The T4 standards should be reconstituted in 2.0 mL distilled water before use.

5. Control Human Sera: These are pools of untreated human sera supplied in freeze-dried form and should be reconstituted in 1.0 mL distilled water. They contain precalibrated free T4 and 0.1% sodium azide and are used to test accuracy of the present assay.
6. Washing Buffer: 100 mL (to be diluted 1:5 with de-ionized or distilled water) containing 0.25M phosphate buffer, pH 7.5, and 0.1% sodium azide.

All reagents should be stored at 2°–8° C. After reconstitution, the free T4 standard can be stored at 2°–8° C. for up to 14 days and the washing buffer for up to 30 days. The control sera should be treated as the serum samples.

All reagents and samples should be brought to room temperature. The working solution is made up and the other freeze-dried reagents are reconstituted by adding the prescribed amount of water, waiting 20 minutes at room temperature and mixing gently. All tests are performed in duplicate.

Each standard, control serum and specimen to be tested in 200 μL aliquots is pipetted into appropriate coated tubes. Reaction buffer (1000 μL) is added to each tube. The tubes are mixed and incubated at room temperature on a horizontal shaker (200–300 rpm) for 1 hour. In this step, the free T4 from the specimen, standard and control serum will be bound to immobilized L1 and therefore immobilized.

Liquid is removed thoroughly from all tubes by aspiration and the tubes are rinsed twice with 1 mL of diluted washing buffer. Liquid is aspirated after each wash. Labelled analyte preparation (1 mL) is added to each tube and the tubes are mixed and incubated as above. In this step, the dissociating agent will displace free T4 from L1 and it will compete with labelled T4 for binding to L2. Unbound ligand is thoroughly removed by aspiration. The bound radioactivity in each tube is measured ($^{125}$I).

The radioactivity reading for the specimen and control sera is then compared to those for the calibrated standards, and the amount of free T4 in the specimen and control sera is deduced as described in Example 1.

All documents cited herein are incorporated by reference in their entirety.

While the invention has been described in detail and with reference to specific embodiments, it will be apparent to one skilled in the art that various changes and modifications can be made to the invention without departing from its spirit or scope.

We claim:

1. A method for determining the quantity of an analyte present (A) in a free form $A_F$ within a biological fluid, said fluid also containing a bound form $A_B$ of said analyte in equilibrium with said free form, the method comprising the steps of:
   (a) contacting said fluid with a predetermined quantity of a first exogenous ligand (L1), said L1 having the property of not binding the bound form $A_B$, but quantitatively binding the free form $A_F$ and sequestering said A from said biological fluid, whereby an L1/A complex is formed in which the amount of the sequestered analyte A is proportional only to the concentration of the free form $A_F$;
   (b) removing endogenous binding proteins, analyte bound to said endogenous proteins and any unsequestered free analyte present in said fluid;
   (c) in the contemporaneous presence of a predetermined quantity of a second exogenous ligand (L2), said L2 having the property of binding to said analyte A as well as to a labelled analyte (M), contacting the L1/A complex with a predetermined quantity of M and a dissociating agent (D), wherein the binding affinity of L1 for A and M is at least 100 times lower in the presence of D than when D is not present, and wherein said D dissociates the sequestered analyte A from L1 without substantially interfering with the binding of A and M to L2, and incubating for about 1 hour so said dissociated A is able to compete with said labelled analyte M for binding to L2; and
   (d) determining the concentration of $A_F$ either by measuring the quantity of M bound to L2 or by measuring the quantity of unbound M,
   wherein A is selected from the group consisting of thyroxin (T4) and triiodothyronine (T3); and when A is T4, L1 is thyroxin binding globulin protein, L2 is an anti-T4 antibody and D is selected from the group consisting of 8-anilino-1-naphthalenesulphonic acid, sodium salicylate and sodium ethyl-[2-mercaptobenzoate(2-)-O,S]-mercurate(1-); and when A is T3, L1 is a monoclonal anti-T3 antibody, L2 is a polyclonal anti-T3 antibody and D is a solution containing citrate buffer, gelatin and sodium azide.

2. The method of claim 1 wherein L1 and L2 are each fixed to a solid phase and are used in quantities insufficient to affect substantially the equilibrium between free analyte and bound analyte in said biological fluid.

3. A method according to claim 2, wherein the solid phase is stationary, or suspended in said biological fluid or dispersed in said fluid.

4. A method according to claim 2, wherein one or both L1 and L2 are fixed to the solid phase directly or via a binding system.

5. A method according to claim 4, wherein the binding system is a combination streptavidin/biotin or anti-fluorescein antibody/fluorescein.

6. A method according to claim 4, wherein the binding system utilizes a specific anti-species antibody.

7. A method according to any one of claims 1,2,3, or 4–6, wherein M is labelled with a detectable label selected from the group consisting of radioactive atoms, enzymes, chemiluminescent groups and fluorescent groups.

8. A method according to any one of claims 1,2,3, or 4–6, wherein said step (d) is conducted by comparison with the same type of measurements made on a series of standard solutions containing pre-determined concentrations of the same analyte.

9. A method according to claim 1 wherein all the steps are performed in a single container.

10. The method of claim 1 wherein in said step (C) the L1/A complex and said L2 are contacted with said M and said D simultaneously.

11. An assembly for determining the free fraction of an analyte (A) present in a biological fluid, said fluid also containing a quantity of the same analyte bound to one or more endogenous ligands in equilibrium with the free fraction, said assembly comprising:
   (a) a first exogenous ligand (L1) having the property of sequestering said A from said biological fluid;
   (b) a second exogenous ligand (L2) having the property of binding to A;
   (c) labelled analyte M;
   (d) a dissociating agent (D) having the property of selectively dissociating the sequestered analyte from L1 without substantially affecting the binding of A and M to L2;
   (e) a set of calibrated standard solutions for comparison or a correlation between measurements of the label and free analyte content of a biological fluid;
   (f) reaction media comprising washing buffers and reaction buffers; and
   (g) instructions for use;
   wherein A is selected from the group consisting of thyroxin (T4) and triiodothyronine (T3); and when A is T4, L1 is thyroxin binding globulin protein, L2 is an anti-T4 antibody and D is selected from the group consisting of 8-anilino-1-napthalenesulphonic acid, sodium salicylate and sodium ethyl-[2-mercaptobenzoate(2-)-O,S]-mercurate(1-); and when A is T3, L1 is a monoclonal anti-T3 antibody, L2 is a polyclonal anti-T3 antibody and D is a solution containing citrate buffer, gelatin and sodium azide.

12. A method for determining the quantity of a free form of an analyte present within a biological fluid, said fluid also containing a bound form of said analyte in equilibrium with said free form, the method comprising the steps of:
(a) sequestering said free analyte with a predetermined quantity of a first exogenous ligand (L1) said L1 not binding no said bound analyte, but specifically and reversibly quantitatively binding to said free analyte, whereby a L1/A complex is formed in which the amount of the sequestered analyze A is proportional only to the concentration of the free form of A;
(b) removing endogenous binding proteins, analyte bound to said endogenous proteins and any unsequestered free analyte present in said fluid;
(c) in the presence of a predetermined quantity of a second exogenous ligand (L2), said L2 having the property of binding to said analyte as well as to a labelled analyte (M), exposing said L1/A complex and L2 to contact with a predetermined quantity of M and a predetermined quantity of a dissociating agent (D), wherein the binding capacity of L1 for said sequestered analyte and said labelled analyte is at least 100 times lower in the presence of D than when D is not present, and incubating for about 1 hour whereby said agent reverses the binding of said sequestered analyte and said L1 and prevents the binding of said labelled analyte with said L1 while not interfering with the binding of L2 to said sequestered analyte and said labelled analyte, thereby creating an L2/A and an L2/M complex;
(d) after step (c) measuring the quantity of M bound to L2 or measuring the quantity of unbound M, each of which directly correlate to the concentration of free analyte in said biological fluid;
wherein A is selected from the group consisting of thyroxin (T4) and triiodothyronine (T3) and when A is T4, L1 is thyroxin binding globulin protein, L2 is an anti-T4 antibody and D is selected from the group consisting of 8-anilino-1-naphthalenesulphonic acid, sodium salicylate and sodium ethyl-[2-mercaptobenzoate(2-)-O,S]-mercurate(1-); and when A is T3, L1 is a monoclonal anti-T3 antibody, L2 is a polyclonal anti-T3 antibody and D is a solution containing citrate buffer, gelatin and sodium azide.

* * * * *